United States Patent
Matthews

(10) Patent No.: US 9,610,155 B2
(45) Date of Patent: Apr. 4, 2017

(54) INTRAOCULAR LENS LOADING SYSTEMS AND METHODS OF USE

(75) Inventor: Gregory V. Matthews, San Francisco, CA (US)

(73) Assignee: POWERVISION, INC., Belmont, CA (US)

(*) Notice: Subject to any disclaimer, the term of this patent is extended or adjusted under 35 U.S.C. 154(b) by 396 days.

(21) Appl. No.: 13/427,617

(22) Filed: Mar. 22, 2012

(65) Prior Publication Data

US 2012/0245591 A1     Sep. 27, 2012

Related U.S. Application Data

(60) Provisional application No. 61/467,352, filed on Mar. 24, 2011.

(51) Int. Cl.
    *A61F 9/00*          (2006.01)
    *A61F 2/16*          (2006.01)

(52) U.S. Cl.
    CPC .......... *A61F 2/1678* (2013.01); *A61F 2/167* (2013.01); *A61F 2/1662* (2013.01); *A61F 2002/1681* (2013.01); *A61F 2002/1682* (2015.04); *A61F 2002/16905* (2015.04); *A61F 2002/169053* (2015.04)

(58) Field of Classification Search
    USPC .......................................... 606/107; 623/6.12
    See application file for complete search history.

(56) References Cited

U.S. PATENT DOCUMENTS

| | | |
|---|---|---|
| 4,111,995 A | 9/1978 | Nelson |
| 4,251,887 A | 2/1981 | Anis |
| 4,253,199 A | 3/1981 | Banko |
| 4,254,509 A | 3/1981 | Tennant |
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |
| 4,435,855 A | 3/1984 | Pannu |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |

(Continued)

FOREIGN PATENT DOCUMENTS

| | | |
|---|---|---|
| CN | 1200659 A | 12/1998 |
| CN | 1283974 A | 2/2001 |

(Continued)

OTHER PUBLICATIONS

Baughman et al., "Negative poisson's ratios for extreme states fo matter," Science, vol. 288, pp. 2018-2022, Jun. 16, 2000.

(Continued)

*Primary Examiner* — Robert Lynch
(74) *Attorney, Agent, or Firm* — Shay Glenn LLP

(57) ABSTRACT

Intraocular lens loading devices, system, and methods of use. The device and systems can be used to load an intraocular lens into a cartridge, from which it can delivered into a patient's eye. The devices and systems can also be used to simply advance an intraocular lens through any type of loading or delivery device.

7 Claims, 6 Drawing Sheets

(56) References Cited

U.S. PATENT DOCUMENTS

| | | |
|---|---|---|
| 4,575,373 A | 3/1986 | Johnson |
| 4,585,457 A | 4/1986 | Kalb |
| 4,600,004 A | 7/1986 | Lopez et al. |
| 4,604,295 A | 8/1986 | Humphreys |
| 4,615,701 A | 10/1986 | Woods |
| 4,620,954 A | 11/1986 | Singer et al. |
| 4,681,102 A | 7/1987 | Bartell |
| 4,685,921 A | 8/1987 | Peyman |
| 4,685,922 A | 8/1987 | Peyman |
| 4,693,717 A | 9/1987 | Michelson |
| 4,702,244 A | 10/1987 | Mazzocco |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,747,404 A | 5/1988 | Jampel et al. |
| 4,763,650 A | 8/1988 | Haer |
| 4,764,423 A | 8/1988 | Yamaguchi et al. |
| 4,765,329 A | 8/1988 | Cumming et al. |
| 4,781,719 A | 11/1988 | Kelman |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,819,631 A | 4/1989 | Poley |
| 4,834,094 A | 5/1989 | Patton et al. |
| 4,836,201 A | 6/1989 | Patton et al. |
| 4,842,601 A | 6/1989 | Smith |
| 4,848,343 A | 7/1989 | Wallsten et al. |
| 4,862,885 A | 9/1989 | Cumming |
| 4,880,000 A | 11/1989 | Holmes et al. |
| 4,888,012 A | 12/1989 | Horn et al. |
| 4,892,543 A | 1/1990 | Turely |
| 4,902,293 A | 2/1990 | Feaster |
| 4,906,247 A | 3/1990 | Fritch |
| 4,911,158 A | 3/1990 | Weatherly |
| 4,911,714 A | 3/1990 | Poley |
| 4,913,536 A | 4/1990 | Barnea |
| 4,917,680 A | 4/1990 | Poley |
| 4,919,130 A | 4/1990 | Stoy et al. |
| 4,919,151 A | 4/1990 | Grubbs et al. |
| 4,932,966 A | 6/1990 | Christie et al. |
| 4,934,363 A | 6/1990 | Smith et al. |
| 4,946,469 A | 8/1990 | Sarfarazi |
| 4,950,289 A | 8/1990 | Krasner |
| 4,955,889 A | 9/1990 | Van Gent |
| 4,963,148 A | 10/1990 | Sulc et al. |
| 4,988,352 A | 1/1991 | Poley |
| 4,994,082 A | 2/1991 | Richards et al. |
| 4,995,879 A | 2/1991 | Dougherty |
| 4,995,880 A | 2/1991 | Galib |
| 5,007,913 A | 4/1991 | Dulebohn et al. |
| 5,015,254 A | 5/1991 | Greite |
| 5,026,393 A | 6/1991 | Mackool |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,098,439 A | 3/1992 | Hill et al. |
| 5,100,410 A | 3/1992 | Dulebohn |
| 5,123,905 A | 6/1992 | Kelman |
| 5,145,884 A | 9/1992 | Yamamoto et al. |
| 5,145,935 A | 9/1992 | Hayashi |
| 5,152,789 A | 10/1992 | Willis |
| 5,171,241 A | 12/1992 | Buboltz et al. |
| 5,171,266 A | 12/1992 | Wiley et al. |
| 5,176,686 A | 1/1993 | Poley |
| 5,190,552 A | 3/1993 | Kelman |
| 5,200,430 A | 4/1993 | Federman |
| 5,201,763 A | 4/1993 | Brady et al. |
| 5,203,788 A | 4/1993 | Wiley |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,304,182 A | 4/1994 | Rheinish et al. |
| 5,326,347 A | 7/1994 | Cumming |
| 5,354,333 A | 10/1994 | Kammann et al. |
| 5,391,590 A | 2/1995 | Gerace et al. |
| 5,405,386 A | 4/1995 | Rheinish et al. |
| 5,425,734 A | 6/1995 | Blake |
| 5,426,166 A | 6/1995 | Usifer et al. |
| 5,443,506 A | 8/1995 | Garabet |
| 5,444,106 A | 8/1995 | Zhou et al. |
| 5,444,135 A | 8/1995 | Cheradame et al. |
| 5,452,932 A | 9/1995 | Griffin |
| 5,468,246 A | 11/1995 | Blake |
| 5,474,562 A | 12/1995 | Orchowski et al. |
| 5,476,514 A | 12/1995 | Cumming |
| 5,489,302 A | 2/1996 | Skottun |
| 5,494,484 A | 2/1996 | Feingold |
| 5,496,328 A | 3/1996 | Nakajima et al. |
| 5,496,366 A | 3/1996 | Cumming |
| 5,499,987 A | 3/1996 | Feingold |
| 5,506,300 A | 4/1996 | Ward et al. |
| 5,512,609 A | 4/1996 | Yang |
| 5,549,614 A | 8/1996 | Tunis |
| 5,556,400 A | 9/1996 | Tunis |
| 5,562,676 A | 10/1996 | Brady et al. |
| 5,567,365 A | 10/1996 | Weinschenk, III et al. |
| 5,578,081 A | 11/1996 | McDonald |
| 5,582,613 A | 12/1996 | Brady et al. |
| 5,584,304 A | 12/1996 | Brady |
| 5,585,049 A | 12/1996 | Grisoni et al. |
| 5,593,436 A | 1/1997 | Langerman |
| 5,607,433 A | 3/1997 | Polla et al. |
| 5,607,472 A | 3/1997 | Thompson |
| 5,616,148 A | 4/1997 | Eagles et al. |
| 5,620,450 A | 4/1997 | Eagles et al. |
| 5,628,795 A | 5/1997 | Langerman |
| 5,633,504 A | 5/1997 | Collins et al. |
| 5,643,276 A | 7/1997 | Zaleski |
| 5,653,715 A | 8/1997 | Reich et al. |
| 5,665,822 A | 9/1997 | Bitler et al. |
| 5,674,282 A | 10/1997 | Cumming |
| 5,676,669 A | 10/1997 | Colvard |
| 5,697,973 A | 12/1997 | Peyman et al. |
| 5,702,400 A | 12/1997 | Brown et al. |
| 5,702,402 A | 12/1997 | Brady |
| 5,702,441 A | 12/1997 | Zhou |
| 5,716,364 A | 2/1998 | Makker et al. |
| 5,735,858 A | 4/1998 | Makker et al. |
| 5,766,182 A | 6/1998 | McDonald |
| 5,772,666 A | 6/1998 | Feingold et al. |
| 5,774,273 A | 6/1998 | Bornhorst |
| 5,776,138 A | 7/1998 | Vidal et al. |
| 5,776,191 A | 7/1998 | Mazzocco |
| 5,776,192 A | 7/1998 | McDonald |
| 5,800,442 A | 9/1998 | Wolf et al. |
| 5,803,925 A | 9/1998 | Yang et al. |
| 5,810,834 A | 9/1998 | Heyman |
| 5,843,188 A | 12/1998 | McDonald |
| 5,860,984 A | 1/1999 | Chambers et al. |
| 5,868,751 A | 2/1999 | Feingold |
| 5,873,879 A | 2/1999 | Figueroa et al. |
| 5,876,440 A | 3/1999 | Feingold |
| 5,891,931 A | 4/1999 | Leboeuf et al. |
| 5,919,197 A | 7/1999 | McDonald |
| 5,921,989 A | 7/1999 | Deacon et al. |
| 5,928,282 A | 7/1999 | Nigam |
| 5,941,886 A | 8/1999 | Feingold |
| 5,944,725 A | 8/1999 | Cicenas et al. |
| 5,947,974 A | 9/1999 | Brady et al. |
| 5,947,975 A | 9/1999 | Kikuchi et al. |
| 5,947,976 A | 9/1999 | Van Noy et al. |
| 5,964,802 A | 10/1999 | Anello et al. |
| 5,976,150 A | 11/1999 | Copeland |
| 5,984,962 A | 11/1999 | Anello et al. |

(56) References Cited

U.S. PATENT DOCUMENTS

| | | |
|---|---|---|
| 6,001,107 A | 12/1999 | Feingold |
| 6,010,510 A | 1/2000 | Brown et al. |
| 6,013,101 A | 1/2000 | Israel |
| 6,015,842 A | 1/2000 | Leboeuf et al. |
| 6,022,358 A | 2/2000 | Wolf et al. |
| 6,048,348 A | 4/2000 | Chambers et al. |
| 6,059,791 A | 5/2000 | Chambers |
| 6,074,397 A | 6/2000 | Chambers et al. |
| 6,102,539 A | 8/2000 | Tucker |
| 6,117,171 A | 9/2000 | Skottun |
| 6,124,980 A | 9/2000 | Cerbell |
| 6,129,733 A | 10/2000 | Brady et al. |
| 6,139,576 A | 10/2000 | Doyle et al. |
| 6,143,000 A | 11/2000 | Feingold |
| 6,143,001 A | 11/2000 | Brown et al. |
| 6,160,084 A | 12/2000 | Langer et al. |
| 6,176,878 B1 | 1/2001 | Gwon et al. |
| 6,179,843 B1 | 1/2001 | Weiler |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,241,737 B1 | 6/2001 | Feingold |
| 6,248,111 B1 | 6/2001 | Glick et al. |
| 6,251,114 B1 | 6/2001 | Farmer et al. |
| 6,280,449 B1 | 8/2001 | Blake |
| 6,283,975 B1 | 9/2001 | Glick et al. |
| 6,283,976 B1 | 9/2001 | Portney |
| 6,299,641 B1 | 10/2001 | Woods |
| 6,302,911 B1 | 10/2001 | Hanna |
| 6,312,433 B1 | 11/2001 | Butts et al. |
| 6,322,589 B1 | 11/2001 | Cumming |
| 6,334,862 B1 | 1/2002 | Vidal et al. |
| 6,336,932 B1 | 1/2002 | Figueroa et al. |
| 6,342,073 B1 | 1/2002 | Cumming et al. |
| 6,348,437 B1 | 2/2002 | Avery et al. |
| 6,371,960 B2 | 4/2002 | Heyman et al. |
| 6,387,101 B1 | 5/2002 | Butts et al. |
| 6,387,126 B1 | 5/2002 | Cumming |
| 6,388,043 B1 | 5/2002 | Langer et al. |
| 6,398,789 B1 | 6/2002 | Capetan |
| 6,406,481 B2 | 6/2002 | Feingold et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,436,092 B1 | 8/2002 | Peyman |
| 6,443,985 B1 | 9/2002 | Woods |
| 6,447,520 B1 | 9/2002 | Ott et al. |
| 6,450,642 B1 | 9/2002 | Jethmalani et al. |
| 6,464,725 B2 | 10/2002 | Skottun |
| 6,468,282 B2 | 10/2002 | Kikuchi et al. |
| 6,471,708 B2 | 10/2002 | Green |
| 6,488,708 B2 | 12/2002 | Sarfarazi |
| 6,491,697 B1 | 12/2002 | Clark et al. |
| 6,493,151 B2 | 12/2002 | Schachar |
| 6,497,708 B1 | 12/2002 | Cumming |
| 6,503,275 B1 | 1/2003 | Cumming |
| 6,503,276 B2 | 1/2003 | Lang et al. |
| 6,506,195 B2 | 1/2003 | Chambers et al. |
| 6,517,577 B1 | 2/2003 | Callahan et al. |
| 6,537,283 B2 | 3/2003 | Van Noy |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk, III et al. |
| 6,601,956 B1 | 8/2003 | Jean et al. |
| 6,605,093 B1 | 8/2003 | Blake |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,723,104 B2 | 4/2004 | Ott |
| 6,730,123 B1 | 5/2004 | Klopotek |
| 6,733,507 B2 | 5/2004 | McNicholas et al. |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,921,405 B2 | 7/2005 | Feingold et al. |
| 6,923,815 B2 | 8/2005 | Brady et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,014,641 B2 | 3/2006 | Kobayashi et al. |
| 7,060,094 B2 | 6/2006 | Shahinpoor et al. |
| 7,068,439 B2 | 6/2006 | Esch |
| 7,070,276 B2 | 7/2006 | Koretz |
| 7,074,227 B2 | 7/2006 | Portney |
| 7,122,053 B2 | 10/2006 | Esch |
| 7,144,423 B2 | 12/2006 | McDonald |
| 7,156,854 B2 | 1/2007 | Brown et al. |
| 7,217,288 B2 | 5/2007 | Esch et al. |
| 7,241,312 B2 | 7/2007 | Lai et al. |
| 7,247,168 B2 | 7/2007 | Esch et al. |
| 7,247,689 B2 | 7/2007 | Makker et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,335,209 B2 | 2/2008 | Meyer |
| 7,354,451 B2 | 4/2008 | Koch |
| 7,416,300 B2 | 8/2008 | Wei et al. |
| 7,429,263 B2 | 9/2008 | Vaquero et al. |
| 7,438,723 B2 | 10/2008 | Esch |
| 7,453,646 B2 | 11/2008 | Lo |
| 7,485,144 B2 | 2/2009 | Esch |
| 7,494,505 B2 | 2/2009 | Kappelhof et al. |
| 7,637,947 B2 | 12/2009 | Smith et al. |
| 7,675,686 B2 | 3/2010 | Lo et al. |
| 7,753,953 B1 | 7/2010 | Yee |
| 7,759,408 B2 | 7/2010 | Schorzman et al. |
| 7,763,069 B2 | 7/2010 | Brady et al. |
| 7,776,088 B2 | 8/2010 | Shadduck |
| 7,878,655 B2 | 2/2011 | Salvati et al. |
| 7,971,997 B2 | 7/2011 | Hiramatsu et al. |
| 7,988,290 B2 | 8/2011 | Campbell et al. |
| 7,988,292 B2 | 8/2011 | Neal et al. |
| 7,988,293 B2 | 8/2011 | Raymond et al. |
| 8,048,155 B2 | 11/2011 | Shadduck |
| 8,158,712 B2 | 4/2012 | Your |
| 8,162,927 B2 | 4/2012 | Peyman |
| 8,241,355 B2 | 8/2012 | Brady et al. |
| 8,246,631 B2 | 8/2012 | Pynson |
| 8,377,125 B2 | 2/2013 | Kellan |

(56) References Cited

U.S. PATENT DOCUMENTS

| | | |
|---|---|---|
| 8,382,769 B2 | 2/2013 | Inoue |
| 8,403,941 B2 | 3/2013 | Peterson et al. |
| 8,475,526 B2 | 7/2013 | Pynson |
| 8,480,734 B2 | 7/2013 | Kellan et al. |
| 8,613,766 B2 | 12/2013 | Richardson et al. |
| 8,632,589 B2 * | 1/2014 | Helmy .................. A61F 2/167 606/107 |
| 8,758,361 B2 | 6/2014 | Kobayashi et al. |
| 8,888,845 B2 | 11/2014 | Vaquero et al. |
| 8,961,601 B2 | 2/2015 | Biddle et al. |
| 9,005,282 B2 | 4/2015 | Chang et al. |
| 9,034,035 B2 | 5/2015 | Betser et al. |
| 9,226,819 B2 | 1/2016 | Downer |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133167 A1 | 9/2002 | Harish et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0186868 A1 | 9/2004 | Kim |
| 2004/0193263 A1 | 9/2004 | Bryan |
| 2004/0230203 A1 | 11/2004 | Yaguchi |
| 2004/0267359 A1 | 12/2004 | Makker et al. |
| 2005/0021139 A1 | 1/2005 | Shadduck |
| 2005/0033308 A1 | 2/2005 | Callahan et al. |
| 2005/0038446 A1 | 2/2005 | Vanderbilt et al. |
| 2005/0049606 A1 | 3/2005 | Vaquero et al. |
| 2005/0080484 A1 | 4/2005 | Marmo et al. |
| 2005/0090612 A1 | 4/2005 | Soane et al. |
| 2005/0113911 A1 | 5/2005 | Peyman |
| 2005/0125000 A1 | 6/2005 | Tourrette et al. |
| 2005/0125055 A1 | 6/2005 | Deacon et al. |
| 2005/0125056 A1 | 6/2005 | Deacon et al. |
| 2005/0131535 A1 | 6/2005 | Woods |
| 2005/0143750 A1 | 6/2005 | Vaquero |
| 2005/0143751 A1 | 6/2005 | Makker et al. |
| 2005/0147735 A1 | 7/2005 | Lowery et al. |
| 2005/0149057 A1 | 7/2005 | Rathert |
| 2005/0165410 A1 | 7/2005 | Zadno-Azizi et al. |
| 2005/0222577 A1 | 10/2005 | Vaquero |
| 2005/0222578 A1 | 10/2005 | Vaquero |
| 2005/0222579 A1 | 10/2005 | Vaquero et al. |
| 2005/0251253 A1 | 11/2005 | Gross |
| 2005/0251254 A1 | 11/2005 | Brady et al. |
| 2005/0259221 A1 | 11/2005 | Marmo |
| 2005/0264756 A1 | 12/2005 | Esch |
| 2005/0283162 A1 | 12/2005 | Stratas |
| 2005/0283164 A1 | 12/2005 | Wu et al. |
| 2006/0020267 A1 | 1/2006 | Marmo |
| 2006/0020268 A1 | 1/2006 | Brady et al. |
| 2006/0036262 A1 | 2/2006 | Hohl |
| 2006/0069433 A1 | 3/2006 | Nun |
| 2006/0085013 A1 | 4/2006 | Dek et al. |
| 2006/0097413 A1 | 5/2006 | Ghazizadeh et al. |
| 2006/0100703 A1 | 5/2006 | Evans et al. |
| 2006/0116763 A1 | 6/2006 | Simpson |
| 2006/0129129 A1 | 6/2006 | Smith |
| 2006/0134173 A1 | 6/2006 | Liu et al. |
| 2006/0135642 A1 | 6/2006 | Makker et al. |
| 2006/0142780 A1 | 6/2006 | Pynson et al. |
| 2006/0142781 A1 | 6/2006 | Pynson et al. |
| 2006/0158611 A1 | 7/2006 | Piers et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0021831 A1 | 1/2007 | Clarke |
| 2007/0027538 A1 | 2/2007 | Aharoni et al. |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0118216 A1 | 5/2007 | Pynson |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0244561 A1 | 10/2007 | Nun |
| 2007/0265636 A1 | 11/2007 | Huynh |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0027537 A1 | 1/2008 | Gerlach et al. |
| 2008/0033449 A1 | 2/2008 | Cole et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0058830 A1 | 3/2008 | Cole et al. |
| 2008/0065096 A1 | 3/2008 | Kappelhof et al. |
| 2008/0071286 A1 | 3/2008 | Kobayashi et al. |
| 2008/0097460 A1 | 4/2008 | Boukhny et al. |
| 2008/0119865 A1 | 5/2008 | Meunier et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0200921 A1 | 8/2008 | Downer |

(56) References Cited

U.S. PATENT DOCUMENTS

| | | |
|---|---|---|
| 2008/0243247 A1 | 10/2008 | Poley et al. |
| 2008/0269887 A1 | 10/2008 | Cumming |
| 2008/0300680 A1 | 12/2008 | Joshua |
| 2008/0306587 A1 | 12/2008 | Your |
| 2008/0306588 A1 | 12/2008 | Smiley et al. |
| 2009/0005865 A1 | 1/2009 | Smiley et al. |
| 2009/0018512 A1 | 1/2009 | Charles |
| 2009/0018548 A1 | 1/2009 | Charles |
| 2009/0024136 A1 | 1/2009 | Martin et al. |
| 2009/0027661 A1 | 1/2009 | Choi et al. |
| 2009/0030425 A1 | 1/2009 | Smiley et al. |
| 2009/0076602 A1 | 3/2009 | Ho et al. |
| 2009/0112313 A1 | 4/2009 | Mentak |
| 2009/0118739 A1 | 5/2009 | Kappelhof et al. |
| 2009/0124773 A1 | 5/2009 | Zhou et al. |
| 2009/0149952 A1 | 6/2009 | Shadduck |
| 2009/0171366 A1 | 7/2009 | Tanaka |
| 2009/0204123 A1 | 8/2009 | Downer |
| 2009/0228101 A1 | 9/2009 | Zadno-Azizi |
| 2009/0234366 A1 | 9/2009 | Tsai et al. |
| 2009/0234449 A1 | 9/2009 | DeJuan, Jr. et al. |
| 2009/0248154 A1 | 10/2009 | Dell |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2009/0318933 A1* | 12/2009 | Anderson ............ 606/107 |
| 2009/0319040 A1 | 12/2009 | Khoury |
| 2010/0016963 A1 | 1/2010 | Park |
| 2010/0039709 A1 | 2/2010 | Lo |
| 2010/0063588 A1 | 3/2010 | Park |
| 2010/0094412 A1 | 4/2010 | Wensrich |
| 2010/0131058 A1 | 5/2010 | Shadduck |
| 2010/0131061 A1 | 5/2010 | Callahan et al. |
| 2010/0161049 A1 | 6/2010 | Inoue |
| 2010/0179653 A1 | 7/2010 | Argento et al. |
| 2010/0204705 A1 | 8/2010 | Brown et al. |
| 2010/0228344 A1 | 9/2010 | Shadduck |
| 2010/0228346 A1 | 9/2010 | Esch |
| 2010/0324671 A1 | 12/2010 | Shadduck |
| 2010/0324672 A1 | 12/2010 | Esch et al. |
| 2011/0052020 A1 | 3/2011 | Hildebrand et al. |
| 2011/0118834 A1 | 5/2011 | Lo et al. |
| 2011/0153015 A1 | 6/2011 | Simonov et al. |
| 2011/0208301 A1 | 8/2011 | Anvar et al. |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2011/0313522 A1 | 12/2011 | Hayes |
| 2011/0313523 A1 | 12/2011 | Hayes |
| 2012/0022547 A1 | 1/2012 | Hildebrand et al. |
| 2012/0078361 A1 | 3/2012 | Shadduck |
| 2012/0078363 A1 | 3/2012 | Lu |
| 2012/0078364 A1 | 3/2012 | Stenger |
| 2012/0116506 A1 | 5/2012 | Compertore |
| 2012/0179249 A1 | 7/2012 | Coleman |
| 2012/0221102 A1* | 8/2012 | Tanaka et al. ............ 623/6.12 |
| 2012/0226351 A1 | 9/2012 | Peyman |
| 2012/0253458 A1 | 10/2012 | Geraghty et al. |
| 2012/0253459 A1 | 10/2012 | Reich et al. |
| 2012/0303119 A1 | 11/2012 | Callahan et al. |
| 2012/0330415 A1 | 12/2012 | Callahan et al. |
| 2013/0053954 A1 | 2/2013 | Rao et al. |
| 2013/0060331 A1 | 3/2013 | Shadduck |
| 2013/0184816 A1 | 7/2013 | Hayes |
| 2014/0249625 A1 | 9/2014 | Shadduck |
| 2015/0087743 A1 | 3/2015 | Anvar et al. |
| 2015/0257874 A1 | 9/2015 | Hildebrand et al. |
| 2016/0113761 A1 | 4/2016 | Nishi et al. |
| 2016/0184091 A1 | 6/2016 | Smiley et al. |
| 2016/0184092 A1 | 6/2016 | Smiley et al. |

FOREIGN PATENT DOCUMENTS

| | | |
|---|---|---|
| CN | 1378440 A | 11/2002 |
| CN | 1384727 A | 12/2002 |
| CN | 101039635 A | 9/2007 |
| CN | 101277659 A | 10/2008 |
| CN | 102271622 A | 12/2011 |
| CN | 202288610 A | 7/2012 |
| EP | 0898972 A2 | 3/1999 |
| EP | 1356791 B1 | 4/2006 |
| EP | 1332731 B1 | 8/2007 |
| EP | 1659991 B1 | 5/2009 |
| EP | 2060243 A1 | 5/2009 |
| EP | 2346441 B1 | 3/2013 |
| FR | 2784575 | 4/2000 |
| JP | 07-044938 | 5/1995 |
| JP | 8501715 | 2/1996 |
| JP | 8224295 | 9/1996 |
| JP | 9294754 | 11/1997 |
| JP | 10-206609 | 8/1998 |
| JP | 11-47168 A | 2/1999 |
| JP | 11056998 | 3/1999 |
| JP | 11169391 A | 6/1999 |
| JP | 11276509 | 10/1999 |
| JP | 11332903 A | 12/1999 |
| JP | 2001-502592 A | 2/2001 |
| JP | 2003144387 | 5/2003 |
| JP | 2003-524503 A | 8/2003 |
| JP | 2003530978 | 10/2003 |
| JP | 2006341094 | 12/2006 |
| JP | 2007513715 A | 5/2007 |
| JP | 2007518447 A | 7/2007 |
| JP | 2008-534111 A | 8/2008 |
| JP | 2008531069 | 8/2008 |
| JP | 2008307394 A | 12/2008 |
| JP | 200934451 | 2/2009 |
| SU | 1810052 | 4/1993 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/51338 | 7/2002 |
| WO | WO 2004/010895 A2 | 2/2004 |
| WO | WO 2004/046768 A2 | 6/2004 |
| WO | WO 2004/072689 A2 | 8/2004 |
| WO | WO 2005/018504 A1 | 3/2005 |
| WO | WO 2005/084588 A1 | 9/2005 |
| WO | WO 2006/004707 A2 | 1/2006 |
| WO | WO2006/011937 A2 | 2/2006 |
| WO | WO 2006/047383 A2 | 5/2006 |
| WO | WO 2006/088440 A1 | 8/2006 |
| WO | WO 2007/005529 A2 | 1/2007 |
| WO | WO2007/005692 A1 | 1/2007 |
| WO | WO 2007/030095 A1 | 3/2007 |
| WO | WO 2007/061688 A2 | 5/2007 |
| WO | WO 2007/128423 A1 | 11/2007 |
| WO | WO2007/138564 A1 | 12/2007 |
| WO | WO 2009/100322 A2 | 8/2009 |
| WO | WO 2009/154455 A1 | 12/2009 |
| WO | WO 2011/119334 A1 | 9/2011 |
| WO | WO2012/006186 A2 | 1/2012 |
| WO | WO 2012/129419 A1 | 9/2012 |

OTHER PUBLICATIONS

Baughman, "Avoiding the shrink," Nature, vol. 425, pp. 667, Oct. 16, 2003.

Conlisk, A. T. et al; Mass Transfer and Flow in Electrically Charged Micro- and Nano-channels; Analytical Chemistry, vol. 74; iss. 9; pp. 2139-2150; May 2002.

Dubbelman et al.; The Thickness of the Aging Human Lens Obtained from Corrected Scheimpflug Images; Optometry & Vison Science; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

(56) References Cited

OTHER PUBLICATIONS

Gordon, "Applications of shape memory polyurethanes," Proceedings of the First Intl Conf. on Shape Memory and Superelastic Tech., Asilomar Conference Center, Pacific Grove, CA, USA, pp. 115-120, Mar. 1994.

Gruber et al.; Exhaustive soxhlet extraction for the complete removal of residual compounds . . . ; Journal of Biomedical Materials Research; vol. 53; No. 5; pp. 445-448; Mar. 2000.

Jeon et al., "Shape memory and nanostructure in poly(norbornyl-POSS) copolymers," Polymer International, vol. 49, pp. 453-457, May 2000.

Kim et al., "Polyurethanes having shape memory effects," Polymer, vol. 37, No. 26, pp. 5781-5793, Dec. 1996.

Lakes et al., "Dramatically stiffer elastic composite materials due to negative stiffness phase?," Journal of the Mechanics and Physics of Solids, vol. 50, pp. 979-1009, May 2002.

Lakes et al., "Extreme damping in composite materials with negative-stiffness inclusions," Nature, vol. 410, pp. 565-567, Mar. 29, 2001.

Lakes et al., "Microbuckling instability in elastomeric cellular sollids," J. Materials Science, vol. 28, pp. 4667-4672, Jan. 1993.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, Feb. 2001.

Lakes, "Extreme damping in composite materials with a negative stiffness phase," Physical Review Letters, vol. 86, No. 13, pp. 2897-2900, Mar. 26, 2001.

Lakes, "Lateral deformations in extreme matter," Science, vol. 288, pp. 1976, Jun. 2000; 3 pgs.

Lakes, "Negative poisson's ratio materials," Science, vol. 238, pp. 551, Oct. 23, 1987.

Lakes, "No contractile obligations," Nature, vol. 358, pp. 713-714, Dec. 31, 1992.

Lendlein et al., "Biodegradable, elastic shape-memory polymers for potential biomedical applications", Science; vol. 296; pp. 1673-1676; May 31, 2002.

Lendlein et al., "Shape-memory polymers," Angew. Chem. Int. Ed.; vol. 41; pp. 2034-2057; Jun. 2002.

Li et al., "Crystallinity and morphology of segmented polyurethanes with different soft-segment length," Journal of Applied Polymer Science, vol. 62, pp. 631-638, Oct. 1996.

Liu et al., "Thermomechanical characterization of a tailored series of shape memory polymers," Journal of Applied Medical Polymers, vol. 6, No. 2, Dec. 2002.

Mather et al., "Strain recovery in POSS hybrid thermoplastics," Polymer Preprints, vol. 41, No. 1, pp. 528-529, Feb. 2000.

Metcalfe et al., "Cold hibernated elastic memory foams for endovascular interventions," Biomaterials, vol. 24, pp. 491-497, Feb. 2003.

Qiao et al.; Bio-inspired accommodating fluidic intraocular lens; Optics Letters; vol. 34; No. 20; pp. 3214-3216; Oct. 15, 2009.

Rosales et al.; Pentacam Scheimpflug QuantitativeImaging of the Crystalline Lens andIntraocular Lens; J. Refractive Surgery; vol. 25; pp. 421-428; May 2009.

Takahashi et al., "Structure and properties of shape-memory polyurethane block copolymers," Journal of Applied Polymer Science, vol. 60, pp. 1061-1069, May 1996.

Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.

Tobushi et al., "Thermomechanical properties of shape memory polymers of polyurethane series and their applications," Journal de Physique IV, Colloque C1, vol. 6, pp. 377-384, Aug. 1996.

Vass et al.; Prediction of pseudophakic capsular bag diameter based on biometric variables; J Cataract Refract Surg.; vol. 25; pp. 1376-1381; Oct. 1999.

Wang et al., "Deformation of extreme viscoelastic metals and composites," Materials Science and Enginerring A, vol. 370, pp. 41-49, Apr. 15, 2004.

Wang et al., "Extreme stiffness systems due to negative stiffness elements," American Journal of Physics, vol. 72, No. 1, pp. 40-50, Jan. 2004.

Wang et al., "Stable extremely-high-damping discrete viscoelastic systems due to native stiffness elements," Applied Physics Letters, vol. 84, No. 22, pp. 4451-4453, May 31, 2004.

Wyant et al; "Basic Wavefront Aberration Theory for Optical Metrology," Applied Optics and Optical Engineering, vol. XI; pp. 1, 28-39; Aug. 10, 1992.

Xu et al., "Making negative poisson's ratio microstructures by soft lithography," Advanced Materials, vol. 11, No. 14, pp. 1186-1189, Jun. 1999.

Matthews et al.; U.S. Appl. No. 13/835,876 entitled "Intraocular Lens Delivery Systems and Methods of Use," filed Mar. 15, 2013.

Langenbucher et al., "Computerized calculation scheme for toric intraocular lenses," Acta Ophthalmologica Scandinavica, vol. 82, No. 3, pp. 270-276, Jun. 2004.

Smiley et al.; U.S. Appl. No. 13/672,608 entitled "Accommodating Intraocular Lenses and Methods of Use," filed Nov. 8, 2012.

Smiley et al.; U.S. Appl. No. 13/711,552 entitled "Accommodating Intraocular Lenses and Methods of Use," filled Dec. 11, 2012.

Lakes; Deformations in extreme matter; Science; perspectives; vol. 288; No. 5473; pp. 1976-1977; Jun. 16, 2000.

Hildebrand et al.; U.S. Appl. No. 13/899,376 entitled "Lens Capsule Size Estimation," filed May 21, 2013.

Esch et al.; U.S. Appl. No. 13/909,946 entitled "Accommodating Intraocular Lenses," filed Jun. 4, 2013.

Hildebrand et al.; U.S. Appl. No. 14/163,794 entitled "Intraocular Lens Delivery Devices and Methods of Use," filed Jan. 24, 2014.

Matthews et al.; U.S. Appl. No. 14/637,171 entited "Intraocular lens delivery systems and methods of use," filed Mar. 3, 2015.

Shadduck; U.S. Appl. No. 14/675,245 entitled "Intraocular lens system and method for power adjustment," filed Mar. 31, 2015.

Matthews; U.S. Appl. No. 14/776,752 entitled "Intraocular lens storage and loading devices and methods of use," filed Sep. 15, 2015.

Smith et al.; U.S. Appl. No. 15/000,783 entitled "Accommodating intraocular lens system having spherical aberration compensation and method," filed Jan. 19, 2016.

\* cited by examiner ns
INTRAOCULAR LENS LOADING SYSTEMS AND METHODS OF USE

CROSS REFERENCE TO RELATED APPLICATIONS

This application claims the benefit of U.S. Provisional Application No. 61/467,352, filed Mar. 24, 2011, the disclosure of which is incorporated by reference herein.

This application is related to U.S. application Ser. No. 12/178,565, filed Jul. 23, 2008, Publication No. 2009-0030425; U.S. application Ser. No. 13/180,427, filed Jul. 11, 2011, Publication No. 2012-002547; U.S. Provisional Application No. 61/613,929, filed Mar. 21, 2012; and U.S. Provisional Application No. 61/557,237, filed Nov. 8, 2011. The disclosure of each of these applications is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

A variety of intraocular lens loading and delivery devices, systems, and methods of use have been described in recent years. Many of them fail to adequately protect the intraocular lens from damage during at least a portion of the loading or delivery of the lens. This can be particularly true if the lens undergoes some degree of deformation during the loading or delivery of the lens, if portions of the lens are relatively delicate and are susceptible to damage during loading or delivery, or if the lens has at least portions that are coupled together and the connections might be susceptible to damage during loading or delivery.

Loading and delivery devices, systems, and method of use are needed that can effectively load or deliver an intraocular lens without damaging the lens.

SUMMARY OF THE DISCLOSURE

A first aspect of the disclosure is a method of loading a fluid-filled intraocular lens into a delivery or storage device, comprising: providing a fluid-filled intraocular lens comprising an optic portion and a peripheral portion; applying loading forces with a loading instrument on the optic portion and on a first portion of the peripheral portion that is less flexible than a second portion of the peripheral portion, wherein the method of loading does not apply a loading force on the second portion of the peripheral portion; and loading the intraocular lens into a delivery or storage device using the loading instrument.

In some embodiments applying the loading forces comprises applying a loading force to the optic portion with a first surface of the loading instrument and applying a loading force to the first portion of the peripheral portion with a second surface of the loading instrument. The first surface can be distal to the second surface. The first surface can be on a first side of the loading instrument and the second surface can be on a second side of the loading instrument.

In some embodiment applying loading forces comprises applying generally distally directed forces on a side of the optic portion and on the first portion of the peripheral portion.

In some embodiments loading comprises deforming at least a portion of the lens.

In some embodiments the peripheral portion is in fluid communication with the optic portion, and wherein the first portion of the peripheral portion is coupled to the optic portion and the second portion of the peripheral portion extends from the first portion.

In some embodiments the method further comprises positioning the intraocular lens in a lens receiving area created by a loading instrument distal region and a loading tray such that a first haptic extends distally relative to the optic portion and a trailing haptic extends proximally relative to the optic portion, wherein the first portion of the peripheral portion is a buttress of the first haptic and the second portion extends from the buttress and is adapted to engage a capsular bag.

In some embodiments the method further comprises positioning a loading instrument distal portion relative to a loading tray so that the loading instrument distal portion and the loading tray create an intraocular lens positioning region, and positioning the intraocular lens in the lens positioning region prior to applying the loading forces.

One aspect of the disclosure is a method of loading a fluid-filled intraocular lens into a delivery or storage device, comprising: providing a fluid-filled intraocular lens comprising an optic portion and a first haptic, the first haptic comprising a connection portion coupled to the optic portion and a second portion extending from the connection portion; applying a loading force with a loading instrument on the optic portion and on the connection portion of the first haptic without applying a loading force on the second portion of the first haptic; and loading the intraocular lens into a delivery or storage device.

In some embodiments the method further comprises positioning the fluid-filled intraocular lens in a lens positioning area of a loading device.

In some embodiments applying the loading forces comprises applying a loading force on the optic portion with a first surface of the loading instrument and applying a loading force on the connection portion with a second surface of the loading instrument. The first surface can be distal to the second surface. The first surface can be on a first side of the loading instrument and the second surface can be on a second side of the loading instrument.

In some embodiments applying loading forces comprises applying generally distally directed forces on the optic portion and the connection portion.

In some embodiments loading comprises deforming at least a portion of the lens.

In some embodiments the method further comprises positioning the intraocular lens in a lens positioning area created by a loading instrument distal region and a loading tray such that the first haptic extends proximally relative to the optic portion and a leading haptic extends distally relative to the optic portion.

One aspect of the disclosure is a method of preparing a fluid-filled intraocular lens for deformation into a delivery or storage device: positioning a plunger distal portion relative to a loading tray so that the plunger distal portion and the loading tray create an intraocular lens positioning region; and positioning an intraocular lens in the lens positioning region so that a lens engaging surface of the plunger distal portion is disposed relative to the fluid-filled optic portion so that the lens engaging surface is positioned to apply a loading force on the fluid-filled optic portion.

In some embodiments positioning the intraocular lens comprises positioning the intraocular lens so that the lens engaging surface of the plunger distal portion is positioned distal to a trailing haptic of the intraocular lens.

In some embodiments positioning the intraocular lens comprises positioning the intraocular lens so that a second lens engaging surface of the plunger is disposed relative to a haptic connection portion of the intraocular lens so that the second lens engaging surface is adapted to apply a loading force on the haptic connection portion.

In some embodiments positioning the intraocular lens comprises positioning the intraocular lens so that a trailing haptic extends proximally from the optic portion. Positioning the intraocular lens can comprise positioning the intraocular lens so that the lens engaging surface of the plunger distal portion is positioned distal to the trailing haptic of the intraocular lens. Positioning the intraocular lens can comprise positioning the intraocular lens so that a leading haptic extends distally from the optic portion.

In some embodiments positioning the intraocular lens comprises positioning the intraocular lens so that a second lens engaging surface of the plunger distal portion is disposed relative to a haptic connection portion so that the second lens engaging surface is adapted to apply a loading force on the haptic connection portion without applying a loading force on a haptic body portion that extends from the haptic connection portion. The lens engaging surface can be disposed distal relative to the second lens engaging surface.

One aspect of the disclosure is a method of preparing a fluid-filled intraocular lens for deformation into a delivery or storage device, comprising: positioning a plunger distal portion relative to a loading tray so that the plunger distal portion and the loading tray create an intraocular lens positioning region; and positioning an intraocular lens in the lens positioning region so that a first lens engaging surface of the plunger distal portion is disposed relative to a fluid-filled optic portion of the intraocular lens so that it can apply a loading force on the fluid-filled optic portion, and so that a second lens engaging surface of the plunger is disposed relative to a peripheral portion of the intraocular lens so that it can apply a loading force on the peripheral portion of the intraocular lens.

In some embodiments positioning the intraocular lens comprises positioning the intraocular lens so that the first lens engaging surface of the plunger distal portion is positioned distal to a trailing haptic of the intraocular lens.

In some embodiments positioning the intraocular lens comprises positioning the intraocular lens so that the second lens engaging surface of the plunger is disposed relative to a haptic connection portion of the intraocular lens so that the it can apply a loading force on the haptic connection portion.

In some embodiments positioning the intraocular lens comprises positioning the intraocular lens so that a trailing haptic extends proximally from the optic portion. Positioning the intraocular lens can comprise positioning the intraocular lens so that the first lens engaging surface of the plunger distal portion is positioned distal to the trailing haptic of the intraocular lens. Positioning the intraocular lens can comprise positioning the intraocular lens so that a leading haptic extends distally from the optic portion.

In some embodiments the first lens engaging surface is disposed distal relative to the second lens engaging surface.

One aspect of the disclosure is a method of deploying a fluid-filled intraocular lens from a delivery device, comprising: applying a loading force on an optic portion of a fluid-filled intraocular lens to load the intraocular lens into a cartridge; and advancing the intraocular lens out of the cartridge solely by delivering a fluid through the cartridge.

In some embodiments the method further comprises applying a loading force on a first portion of a peripheral portion of the intraocular lens that is less flexible than a second portion of the peripheral portion of the intraocular lens.

In some embodiments the method further comprises applying a loading force on a haptic connection portion that is less flexible than a haptic body portion without applying a loading force on the haptic body portion.

One aspect of the disclosure is a loading instrument adapted to advance an intraocular lens through a loading device, comprising: an elongate portion and a distal lens engaging portion extending distally from the elongate portion, the distal lens engaging portion comprising a first lens engaging surface adapted to engage an optic portion and a second lens engaging surface adapted to engage a peripheral portion of the intraocular lens.

In some embodiments the first lens engaging surface is positioned distal to the second lens engaging surface.

In some embodiments the first lens engaging surface is disposed on a first side of the loading instrument and the second lens engaging surface is disposed on a second side of the loading instrument.

In some embodiments the distal lens engaging portion comprises a generally flat base portion, and wherein the first and second lens engaging surfaces extend from the base portion. The base portion can be substantially perpendicular to the first and second lens engaging surfaces.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which.

DETAILED DESCRIPTION OF THE DISCLOSURE

The disclosure herein relates to intraocular lens loading systems and methods of use. The systems can be used to load an intraocular lens into a delivery device or to advance the lens through any type of medical device. The systems can be used to deliver an intraocular lens into a patient's eye. The systems can be used to both load an intraocular lens into a delivery device and deliver the intraocular lens into the patient's eye.

An intraocular lens is typically implanted within a patient's eye to replace the function of an eye's native lens. The native lens can become diseased (e.g., cataract), or the lens can lose the ability to accommodate over time (i.e., presbyopia). In either case, the native lens can be removed and replaced with an intraocular lens. To deliver the lens through as small an incision as reasonable, the lens typically undergoes some type of deformation during the loading and/or delivery process to reduce the profile of the lens. Additionally, some intraocular lenses include components that can be reconfigured relative to other components, and the controlled positioning or deformation of these components during the loading and/or delivery steps can enhance the loading and/or delivery.

The loading systems described herein can be used to load or advance ocular implants such as intraocular lenses, and can be flexible non-accommodating intraocular lenses or accommodating intraocular lenses. The implants have at least one component that can be reconfigured or deformed during the loading and/or delivery steps. In some embodiments the loading systems can be used to load and deliver accommodating intraocular lenses that have one or more flowable media therein. For example, the loading systems can be used to load and deliver fluid-filled accommodating intraocular lenses, while in some embodiments the lens can comprise a low viscosity polymeric material.

Exemplary fluid-filled accommodating intraocular lenses with one or more haptics that can be loaded and/or delivered using the systems herein are described in U.S. Provisional Application. No. 61/557,237, filed Nov. 8, 2011, U.S. Pat. No. 7,122,053, U.S. Pat. No. 7,261,737, U.S. Pub. No. 2007/0203578, U.S. Pat. No. 7,637,947, U.S. Pat. No. 7,247,168, U.S. Pub. No. 2008/0306588, U.S. Pub. No. 2009/0005865, U.S. Pat. No. 7,857,850, and U.S. Pub. No. 2009/0264998, the disclosures of which are incorporated by reference herein. Additional features and details of loading and/or delivering a lens that can be incorporated into the disclosure herein can be found in U.S. Pub. No. 2009/0030425, the disclosure of which is incorporated by reference herein.

Figure 1:
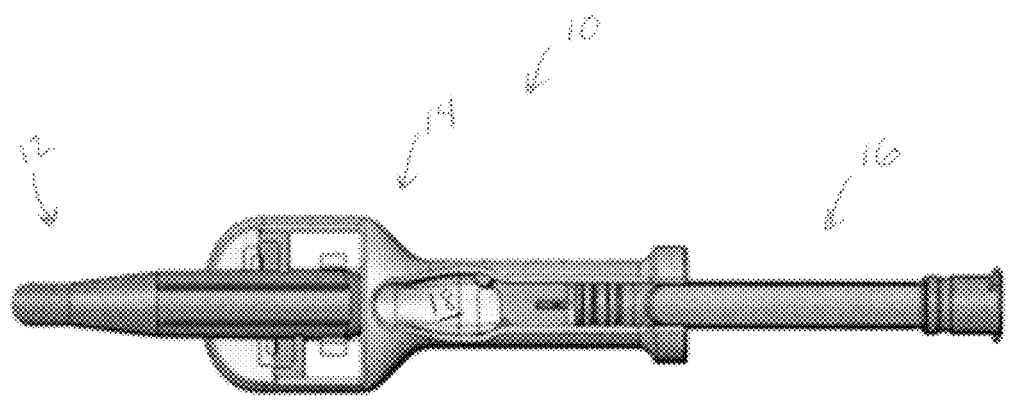
FIG. 1 shows an exemplary system for at least loading an intraocular lens into a cartridge

FIG. 1 illustrates an exemplary intraocular lens loading system. Lens loading system 10 includes cartridge 12, loading tray 14, and plunger 16. In general, plunger 16 and loading tray 14 are configured to load an intraocular lens into cartridge 12. Once in cartridge 12, the lens can be kept there for any length of time (including storage), or the lens may be delivered shortly thereafter from cartridge 12 into a patient. Cartridge 12 is positioned with respect to loading tray 14 such that cartridge and loading tray 14 are in secured engagement. In some embodiments cartridge 12 and loading tray 14 are integral such that cartridge 12 is not adapted to be disassociated from loading tray 14. In some embodiments cartridge 12 shown need not be part of the system, such that the system comprises the loading tray and plunger without a cartridge. When plunger 16 is positioned within loading tray 14 in the position as shown in FIG. 1, the distal portion of plunger 16 and one or more inner surfaces of loading tray 14 create lens positioning region 18, which is adapted to receive an implant therein that is to be loaded into cartridge 12.

Figure 2A:
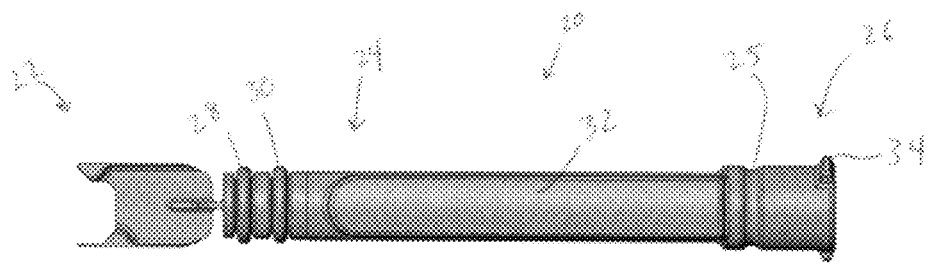
FIGS. 2A and 2B illustrate an exemplary loading instrument.
Figure 2B:
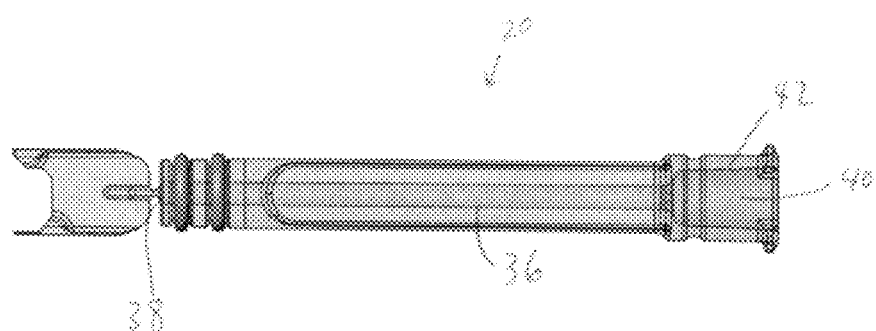
Figure 3:
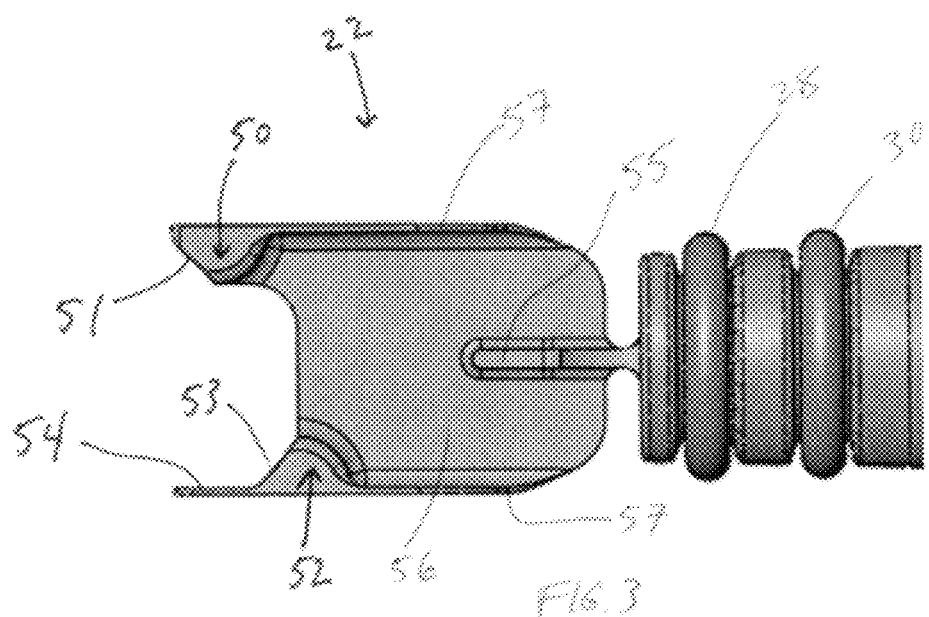
FIG. 3 shows a detailed view of a distal region of the loading instrument from FIGS. 2A and 2B.

FIGS. 2A and 2B illustrate an exemplary loading instrument in the form of plunger 20. Plunger 20 includes distal lens interface portion 22, proximal portion 26, and central portion 24 extending between distal portion 22 and proximal portion 26. Distal lens interface portion 22 is generally the portion that interfaces with the implant and portions of which are adapted to apply one or more loading forces on one or more portions of the intraocular lens, details of which are shown in FIG. 3. Plunger 20 includes seals 28 and 30 shown as O-rings. The central portion includes keying element 32, which is adapted to interact with a loading tray channel to restrict rotation of the plunger with respect to the loading tray. Keying element 32 is shown as a region of the plunger that is raised with respect to adjacent regions of the plunger housing. Key element 32 resists rotation of the plunger when, for example, tightening a leur lock syringe to the proximal end of the plunger, as described below. It also acts as the loading tray plug that occupies space in the loading tray channel to make the handpiece circular for handling ergonomics. Plunger 20 also includes detent 25, which is adapted to interact with the loading tray and prevent movement therebetween. The detent acts as a positive stop feature to indicate to an operator that the lens has been fully advanced with respect to the cartridge. The detent also acts as a safety against the cartridge/loading tray assembly moving forward relative to the plunger as pressure is developed behind the lens during delivery. Proximal portion 26 also includes a leur lock 34, which is adapted to secure the loading tray with a syringe, which is described below.

FIG. 2B shows plunger 20 (similar components from FIG. 2A not labeled for clarity) having an internal lumen defined by inner surface 36 extending through the central portion of plunger 20. In the proximal region of the plunger, lumen wall 36 radially extends to receiving wall 42, which defines receiving area 40. In some embodiments described below the receiving area is adapted to receive a distal portion of a syringe. Lumen wall 36 extends through the plunger to distal port 38, such that the lumen extending through the plunger allows lens distal interfacing portion 22, and any lens positioned therein, to be in fluid communication with the proximal region of the plunger. In some embodiments viscoelastic fluid or other types of fluid can be advanced through the plunger lumen from the proximal end using a syringe.

FIG. 3 illustrates distal portion 22 and a portion of central portion 24 of plunger 20 from FIGS. 2A and 2B. Lens interfacing portion 22 includes base 56, side walls 57 and protrusions 50 and 52. Base 56 provides axial stiffness while maintaining contact with the lens during a portion of the loading process in which the lens is folded (described below). Protrusion 50 is positioned further distally than protrusion 52, and lens engaging surface 51 is disposed further distally than lens engaging surface 53. Stated alternatively, the lens contact surfaces are asymmetrical. Protrusions 50 and 52 include lens engaging surfaces 51 and 53, respectively, which are each adapted to engage a portion of the ocular implant and apply a loading force on a portion of the implant. Lens engaging surfaces 51 and 53 are generally flattened surfaces, but can have other surface shapes or configurations as well. Lens engaging surfaces 51 is disposed on one side of the distal portion 22 while lens engaging surface 53 is disposed on the other side of distal portion 22. The surfaces 51 and 53 are generally perpendicular to the base surface 56. Extending axially from lens engaging surface 53 is tab 54, which has a generally flat configuration. The tab provides sliding support for a portion of the implant, such as a haptic. Lens interfacing portion 22 also includes rib 55, which reduces the potential of longitudinal buckling of base 56. Also shown are seals 28 and 30 of the plunger.

Figure 4:
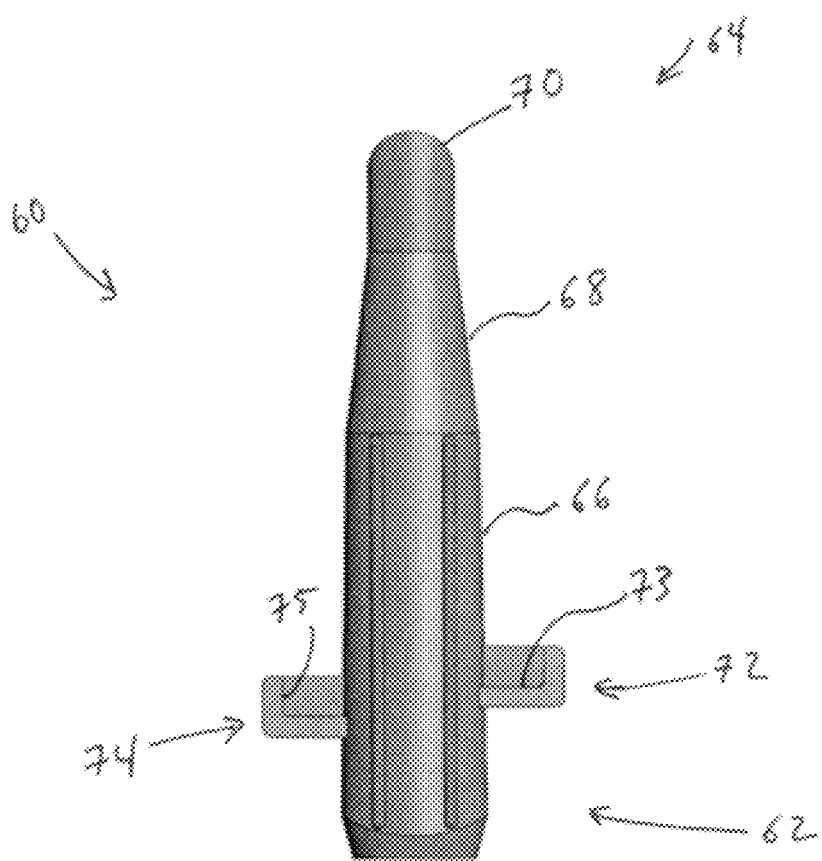
FIG. 4 illustrates an exemplary cartridge.

FIG. 4 illustrates an exemplary cartridge 60. Cartridge 60 includes proximal end 62 and distal end 64. Cartridge 20 has a lumen extending therein from the proximal end to the distal end through which a lens can be advanced. The cartridge includes proximal portion 66, tapering central portion 68, and distal portion 70. The lens is ejected from cartridge 60 out of distal portion 70. Proximal portions 66 and distal portions 70 have generally uniform inner diameters. Distal portion 70 has a curvilinearly shaped distal end. Cartridge 60 also includes locking features 72 and 74, with engaging surfaces 73 and 75. Locking features 72 and 74 are adapted to securingly engage elements on the loading tray to securingly engage the cartridge to the loading tray.

In some embodiments the implant is an intraocular lens that is to be delivered into the patient's eye to replace the native lens. The intraocular lens can be accommodating or non-accommodating. A non-accommodating intraocular lens can be adapted to be deformed when being loaded with the delivery systems, but is adapted to remain undeformed when implanted within an eye to provide a single power implant when implanted within the eye. In the exemplary method of use below a delivery system is used to load and deliver an intraocular lens with an optic portion and a peripheral portion. The peripheral portion includes two haptics that are coupled to the optic portion and which extend radially from the optic portion. The haptics can be a deformable or flexible material, such as a deformable polymeric material. The loading system can be used with a fluid-filled accommodating intraocular lens wherein the haptics are in fluid communication with the optic portion, such as in the accommodating intraocular lenses incorporated by reference above.

Figure 5A:
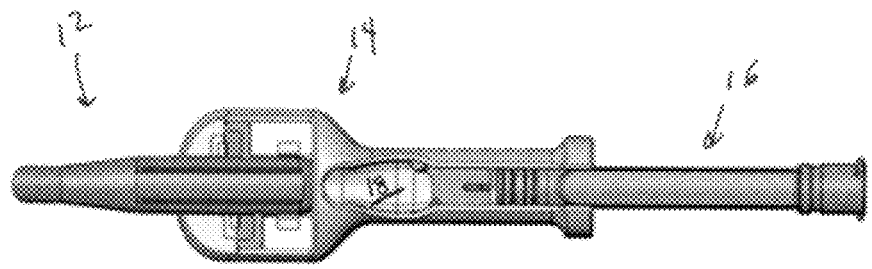
FIGS. 5A and 5B illustrate an exemplary loading instrument positioned relative to a loading tray to create a lens positioning area.
Figure 5B:
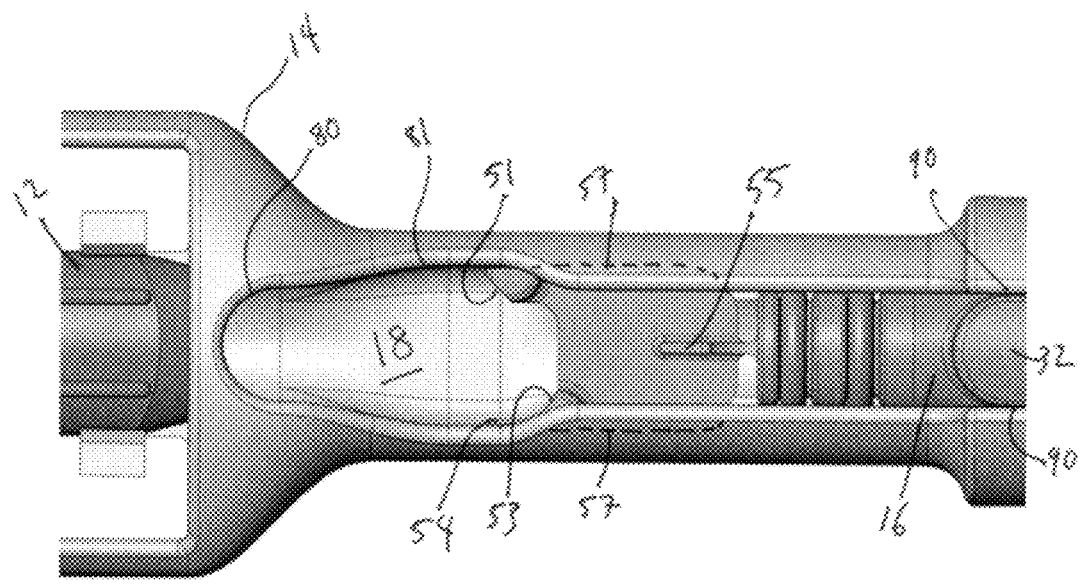

FIG. 5A shows the system from FIG. 1 in a configuration ready to receive an implant for loading into the cartridge. The loading instrument, in the form of plunger 16, has been positioned relative to loading tray 14 so that the plunger distal portion and the loading tray create an intraocular lens positioning region. System 10 includes cartridge 12 securingly engaged with loading tray 14, and plunger 16 is disposed within loading tray 14 to provide lens positioning region 18. FIG. 5B is a close-up view of lens positioning region 18 and distal portion 22 of plunger 16. As shown in FIG. 5B, plunger 16 has been advanced within loading tray 14, wherein the engagement between tray channel wall portion 90 and keying features 32 prevents the plunger from rotating within the loading tray. Sidewalls 57 of the distal portion 22 of plunger are shown by the dotted lines. Lens contacting surface 51 and tab 54 have been advanced to a proximal region of lens positioning region 18 where tray channel wall portion 81 of loading tray 14 is wider than tray channel wall portions 80 or 90. The channel in loading tray 14 defined by wall portions 80, 81, and 90 allows for the implant to be positioned in lens positioning region 18 as well as for visual inspection of the lens during at least an initial portion of the loading process. The channel wall tapers from portion 81 to portion 80, which helps prevent the implant from being ejected from lens positioning region 18 as it is advanced towards the cartridge.

In an optional step, a lubricating material such as viscoelastic material is injected through the lumen of plunger (see FIG. 2B) from the proximal end to the lens interfacing portion 22 to lubricate lens positioning region 18 in preparation for the positioning of the implant and to lubricate the implant and lens interfacing portion 22 for loading.

Figure 6A:
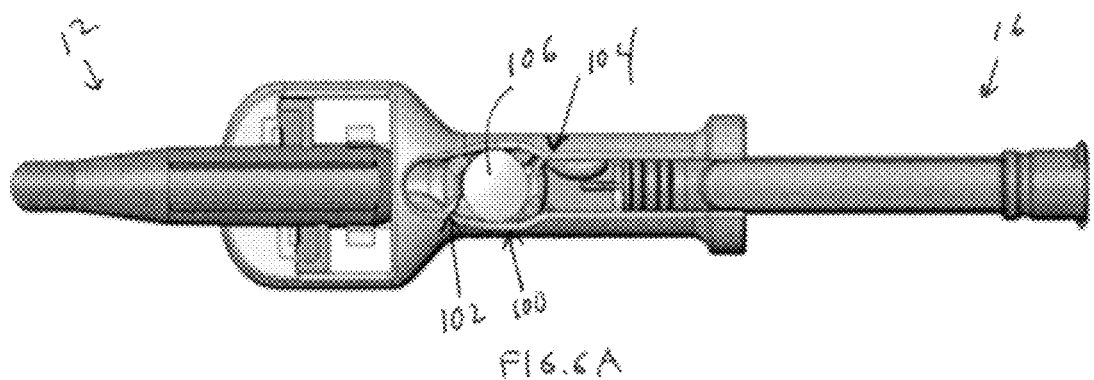
FIGS. 6A-6C illustrate an exemplary fluid-filled intraocular lens positioned in the lens positioning area with lens engaging surfaces adapted to applying loading forces to the optic portion and to a connection portion of the trailing haptic.
Figure 6B:
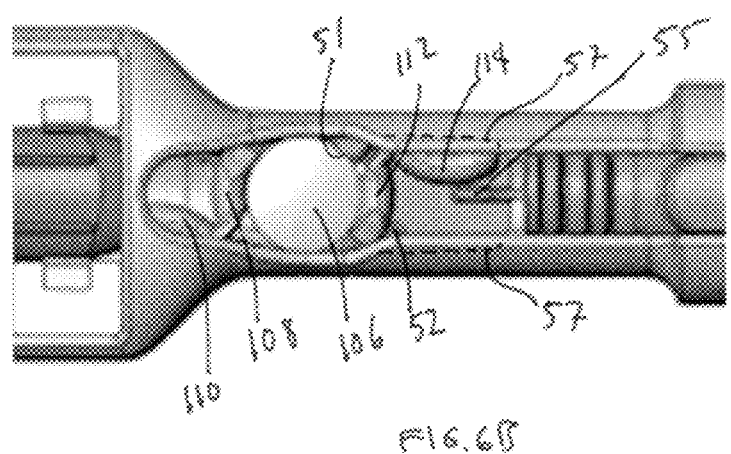
Figure 6C:
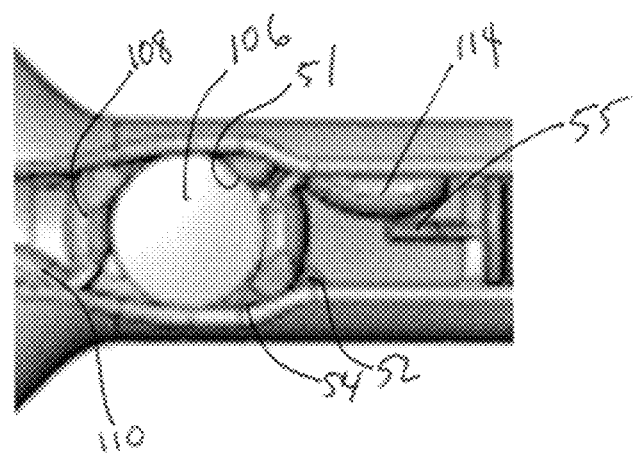

FIGS. 6A, 6B, and 6C (with increasing magnification) illustrate an exemplary manner of positioning an intraocular lens with the lens positioning region shown in FIGS. 5A and 5B. Lens 100 includes an optic portion 106 and a peripheral portion including first peripheral member 102 and second peripheral member 104. First peripheral member 102 is positioned such that it is in a leading position (at least a portion of it extends distally relative to optic 106), while second peripheral member 104 is in a trailing position (at least a portion of it extends proximally relative to optic 106). Leading peripheral portion 102 includes a connection portion 108 (also referred to herein as a "buttress") coupled to the optic portion, and haptic body portion 110 extending from connection portion 108. To load the lens into receiving area, haptic portion 110 is deformed relative to connection portion 108 from a position in which it follows the general curvature of optic 106 to the position shown in FIGS. 6A-6C (i.e., extending distally). This can be performed manually or using another tool. In the figures, haptic body portion 110 is disposed distal to connection portion 108, and engages an inner wall portion of loading tray. The distal portion 22 of plunger is not engaging leading peripheral member 102 in this embodiment. Trailing peripheral member 104 similarly includes a connection portion 112 (which may also be referred to herein as a "buttress") and haptic body portion 114 extending from connection portion 112. The lens has been positioned into the lens positioning region so that lens engaging surface 51 is disposed relative to the optic portion so that surface 51 is positioned to apply a loading force on the optic portion, described below. Lens engaging surface 51 may or may not be in actual contact with optic portion 106, but if it is not it is very near to it and is considered "adjacent" to it. The intraocular lens has also been positioned in the lens positioning region so that lens engaging surface 53 is disposed relative to connection portion 112 so that lens engaging surface 53 can apply a loading force on the connection portion 112. Lens engaging surface 53 may or may not be in direct contact with connection portion 112, but if not it is very near to it and considered to be "adjacent." Neither surface 51 nor 53 is positioned to apply a loading force to either of haptic body portions 110 or 114.

The lens has been positioned in the lens positioning region such that lens engaging surface 51 is distal to the trailing haptic. This allows the loading instrument to be actuated to apply loading forces to the optic (or other less flexible portions) while avoiding the trailing haptic body.

In this embodiment the connection portions 108 and 112 of each haptic are less flexible than haptic body portions 110 and 114. One advantage of the connection portions being stiffer than the body portions is to ensure than the haptics do not disengage from the optic portion, and to ensure that the connection portions do not fail at the connection point with the optic. It is therefore generally safer to apply loading forces to the less flexible connection portions rather than the body portions. In fact, in some instances applying loading forces to the haptic body portions can damage the haptic body portion. The optic, or at least the side of the optic (to which the loading forces are applied) is also less flexible than the haptic body portions, and thus can safely receive the loading force from lens engaging surface 51. Additionally, the loading force on optic 106 is applied to a side of optic rather than either the anterior or posterior optic surfaces. This helps ensure that damage is not done to the optic or its optical surfaces. In this embodiment the lens is positioned so that the loading instrument can apply loading forces to the less flexible portions of the lens, while avoiding the application of loading forces to more flexible portions of the lens.

Tab 54 (not clearly shown) extends distally from protrusion 52 and provides sliding support for buttress 112 during the loading process. Lens contacting surface 51 of protrusion 50 is in contact with a portion of optic 106, as shown in the figures. Haptic portion 114 is folded proximally relative to buttress 112 between sidewall 57 and rib 55.

By positioning peripheral members 102 and 104 relative to optic 106, the manner in which the implant is compressed or deformed during the loading process can be controlled. Additionally, when an intraocular lens comprises one or more fluids therein, controlling the manner in which fluid is redistributed within the lens during loading can be increasingly important to prevent rupturing of the lens.

Figure 7:
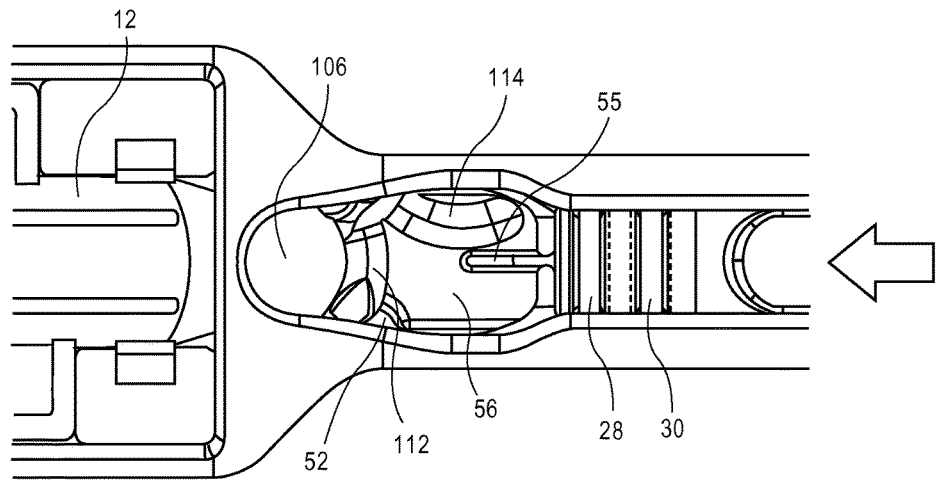
FIG. 7 illustrates an exemplary actuation of the loading instrument, causing loading forces to be applied to the optic and haptic connection portion, thereby loading the intraocular lens into the cartridge.

After lens 100 is positioned within the lens receiving area as shown in FIGS. 6A-6C, an operator loads the intraocular lens into the cartridge. An operator advances the plunger distally within the loading tray, as illustrated in FIG. 7. The actuation of the plunger causes loading forces to be applied to the side of optic 106 and connection portion 112 by lens engaging surfaces 51 and 53, respectively, as set forth above. It should be noted that some non-loading forces may be inherently applied to haptic body portion 114 from the wall of the distal end of plunger. These forces are not, however, considered loading forces as described herein. Because the lens engaging surfaces 51 and 53 apply forces to optic 106 and connection portion 112, and these forces drive the lens movement through the system, they are referred to as loading forces.

Figure 9:
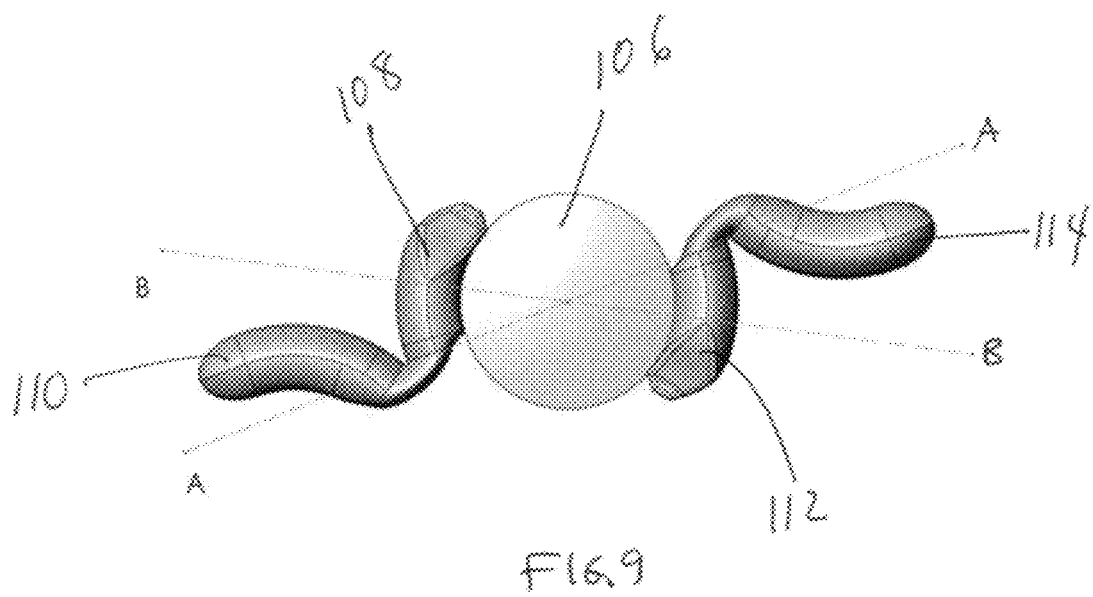
FIG. 9 illustrates exemplary folding axes along which the intraocular lens from FIGS. 6A-7 can fold.

Actuation of plunger advances lens 100 within the loading tray and towards cartridge 12. The plunger, cartridge, and seals (see 28 and 30 in FIG. 7) create a closed path for the lubricating agent from the proximal end of the plunger to the lens interfacing area. As the lens is advanced, the leading peripheral member first enters into cartridge, followed by the optic, and finally by the trailing peripheral member. The distal portion 22 of plunger helps introduce a preferential fold into the lens as it is advanced into cartridge. The lens folding is initiated by ramping and lumen section size restriction while the lens is being advanced. The tray dimensions also influence how the lens will fold. The lens folds generally along a fold axis, but the fold axis is not necessarily a perfectly straight line, and can be thought of as a fold axis along a general direction. FIG. 9 illustrates exemplary folding axes A and B along which the lens from FIGS. 6A-7 may fold. With the system and lens shown, the lens folds generally along axis B, which extends generally through the center of the optic portion and divides the lens into generally symmetrical halves. The axis can also be somewhere in between axis A and axis B. The folded configuration can be described generally, from an end-view of the lens, as a "C" shape, a "U" shape, or a configuration in between. Exemplary intraocular lens described in U.S. Pub. No. 2008/0306588 can be loaded using the systems herein. For example, the lens can include an anterior element, a posterior element, and intermediate layer in between the anterior and posterior elements. In some embodiments the lens folds along the folding axis such that the posterior element forms the backside of the folded configuration, and the intermediate layer and anterior element are collapsed within the posterior element. In other embodiments, the posterior element and intermediate layer are collapsed within the anterior element. In some lenses the optic portion comprises one or more fluid channels in which fluid is adapted to move to actuate the lens. In some embodiments the lens can fold along those channels. In some embodiments axis B is in general alignment with the channels in the lens.

In some embodiments the lens does not have an intermediate layer and the optic portion comprises an anterior surface and a posterior surface defining an optic fluid-filled portion in fluid communication with the haptics. An exemplary lens of this type is described in U.S. Provisional Application No. 61/557,237, filed Nov. 8, 2011, the disclosure of which is incorporated by reference. In these embodiments either the posterior element or the anterior element can form the backside of the folded configuration, collapsing the other element inside of it. In some embodiments of lens design not particularly disclosed herein, the lens can fold along axis A. The fold axis depends on the configuration of the peripheral portion of the lens, the optic configuration, how the peripheral portion is coupled to the peripheral portion, and other factors. Additionally, axis B as shown (along which the shown lens folds) is generally in alignment with the longitudinal axis of the loading tray, and the channel created in the loading tray.

During the loading of the lens into the cartridge, rib 55 provide axial stiffening and reduces the potential for base 56 to longitudinally buckle (see FIG. 3). Base 56 provides axial stiffness while maintaining contact with the lens as the lens is folding during the loading process. The operator continues to advance the plunger (and therefore the lens) until substantially all of the lens is disposed within the cartridge. All of the lens can be advanced into proximal section 66 of cartridge (see FIG. 4), or a portion of the lens (such as a portion of the leading haptic) can be disposed within intermediate portion 68. As the lens is moved into the cartridge, any fluid within the lens is redistributed, or at least the fluid pressure within portions of the lens changes. For example, as the optic portion is deformed, fluid in the optic can be moved towards the peripheral portion, or at least the fluid pressure in the peripheral portion increases. In other embodiments, as the leading haptic is advanced into the cartridge, the fluid is moved towards the optic, or at least the fluid pressure in the optic portion is increased. In other embodiments fluid moves from the trailing haptic towards the leading haptic by means of the pressure differential across the lens body.

Optionally, a lubricating syringe with plunger (not shown), engaged with the leur lock at the proximal end of plunger (see FIG. 2B), is then actuated to advance the syringe plunger with respect to plunger 16 to advance a lubricating agent (such as a viscoelastic material) through plunger and into the cartridge to push the lens forward within the cartridge. This is continued until the leading haptic is disposed at the distal opening of the cartridge. This priming step is optional and is not necessarily performed. For example, in some embodiments the lens can be loaded and then delivered without the optional priming step. Avoiding the priming step in some uses may actually lessen the time that the lens body is in a relatively high compression state. This can potentially reduce time-dependent failures such as pressure-related material failures in the lens as well as sticktion issues between the lens and the cartridge.

At this point the lens can stored in the cartridge for future implantation, or the lens can be delivered into the patient following the loading process into the cartridge. If it is to be stored, the cartridge can be released from the loading tray by disengaging the locking elements. When the lens is to be delivered, an incision is made in the patient's eye to allow for the distal tip of the cartridge to be positioned within the incision (the incision can be made at any point relative to the occurrence of any of the loading and delivery steps). The incision can be a scleral incision, and techniques for making a scleral incision are known. The incision is generally from about 3.8 mm to about 5.5 mm, and in some embodiments is about 4 mm to about 5 mm. In some embodiments the incision is about 4 mm, and in some embodiments the incision is about 5.2 mm. To deliver the lens, the syringe plunger is again advanced (or if the priming step above is not performed, the syringe plunger is advanced for the first time) to push viscoelastic material through the cartridge, forcing the implant from the distal port of the cartridge and into the target location within the eye. Varying the cartridge material and fluid delivery velocity allows for a variety of fluids to be used to deliver the lens from the cartridge. For example, using a given combination of cartridge material and fluid velocity, a low viscosity fluid such as saline can be used to deliver the lens from the cartridge.

In this way the viscoelastic material is all that is needed to force the lens from the cartridge into the eye (although other forces could be used). The leading haptic is delivered first, followed by the optic, and then the trailing haptic. In some embodiments the lens is delivered into a native capsule from which the native lens has been removed. In some embodiments the lens is delivered outside the native capsule from which the native lens has been removed. In some embodiments the lens can be delivered into the anterior chamber.

One aspect of the disclosure is a method of deploying a fluid-filled intraocular lens from a delivery device, comprising applying a loading force on an optic portion of a fluid-filled intraocular lens to load the intraocular lens into a cartridge, and advancing the intraocular lens through the cartridge solely by delivering a fluid (e.g., viscoelastic) through the cartridge.

An additional advantage of the loading systems described herein is that the orientation of the lens relative to the anatomy of the eye can be controlled during loading and/or delivery. In FIGS. 6A-7, an anterior surface of the optic is shown "facing up" in the figures. The posterior surface is facing down, and cannot be seen in the figures. When loaded anterior-up, it will be delivered from the system in the same orientation—anterior-up, and will not roll as it is being advanced through the cartridge. This gives the operator confidence that they will know the orientation of the lens as it is deployed. This can be important because the operator (e.g., a surgeon) generally wants to deliver an intraocular lens into the eye in a known orientation relative to the rest of the eye. For example, when an intraocular lens is being delivered within a native capsule, for which the native lens has been removed, the operator may want to deliver the intraocular lens such that anterior surface of the intraocular lens faces in the anterior direction and the posterior surface of the intraocular lens faces in the posterior direction. Stated alternatively, it may be beneficial to deliver the intraocular lens substantially in the same plane as the capsular bag.

Even when an intraocular lens does not have dedicated anterior and posterior surfaces (i.e., either surface can be delivered facing in the anterior direction and either surface can be delivered facing in the posterior direction), the systems herein still provide the advantage that the anterior and posterior surfaces of the lens will be delivered in substantial alignment with the plane of the capsular bag, and that the lens will not undergo substantial "roll" as it is advanced through the loading system. This can still provide the advantage that the operator knows the overall relative orientation of the lens as it is delivered. Again the operator will know that they do not have to rotate the system in order to deliver the lens in a desired orientation.

Figure 8:
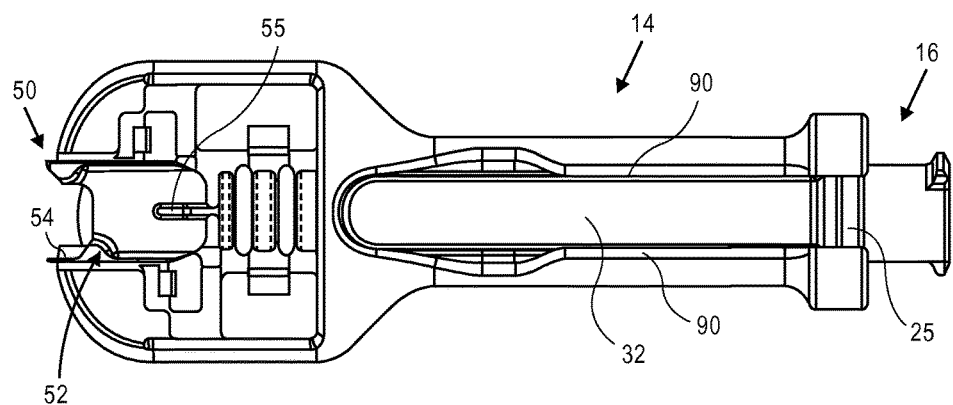
FIG. 8 illustrates a loading tray and a loading instrument after the loading instrument has been advanced such that the loading instrument distal portion is in the distal portion of the loading tray.

FIG. 8 illustrates loading tray 14 and plunger 16 when plunger is advanced such that the plunger lens interfacing portion is in the distal portion of loading tray 14. Detent 25 (see FIG. 2A) interacts with loading tray to prevent relative movement between tray 14 and plunger 16.

It should be noted that not all of the method steps described in the exemplary method of loading and delivery need to be performed. For example, the lens could be delivered from the cartridge by first disengaging the tray from the cartridge, then advancing a small plunger through the cartridge to deliver the lens from the cartridge.

Additionally, lenses can be loaded using the systems described herein even if their peripheral portions do not have the same shape and/or configurations as described herein, if the loading of such lenses can be improved by using the systems herein. Additionally, a lens can have more or less than two peripheral members and still be loaded and delivered using the systems herein. For example, a lens could have only one peripheral portion and could be loaded as the trailing peripheral portion. In this exemplary embodiment there would be no leading peripheral member, simply the optic portion and the trailing haptic. Or, alternatively, a lens could be delivered with more than two peripheral portions as long as the third (or more) peripheral portions do not interfere with the loading.

What is claimed is:

1. A method of loading a fluid-filled intraocular lens into a delivery or storage device, comprising:
   providing a fluid-filled intraocular lens comprising an optic portion and a first haptic, the first haptic comprising a connection portion coupled to the optic portion and a second portion extending from the connection portion;
   while the second portion is deformed, relative to the connection portion, from a position in which it follows the general curvature of the optic portion to a position in which it extends further away from the optic portion, applying a loading force with a loading instrument on the connection portion of the first haptic without applying a loading force on the second portion of the first haptic; and
   loading the intraocular lens into a delivery or storage device.

2. The method of claim 1 further comprising positioning the fluid-filled intraocular lens in a lens positioning area of a loading device.

3. The method of claim 1 wherein applying the loading force comprises applying a generally distally directed force directly on the connection portion with the loading instrument.

4. The method of claim 1 wherein loading comprises deforming at least a portion of the lens.

5. The method of claim 1 wherein applying a loading force with a loading instrument on the connection portion of the first haptic comprises directly engaging the loading instrument with the connection portion of the first haptic.

6. The method of claim 1 wherein applying the loading force comprises applying the loading force while the second portion extends proximally relative to the optic portion.

7. The method of claim 1 wherein applying the loading force on the connection portion does not re-orient the connection portion with respect to the optic portion.

* * * * *